(12) United States Patent
Holcomb

(10) Patent No.: US 6,741,889 B1
(45) Date of Patent: *May 25, 2004

(54) ELECTRONIC APPARATUS AND METHOD FOR TREATING HUMAN PAIN THROUGH APPLICATION OF AN ELECTRICAL STIMULUS IN COMBINATION WITH APPLICATION OF A MAGNETIC FIELD

(75) Inventor: Robert R. Holcomb, Nashville, TN (US)

(73) Assignee: Holcomb Healthcare Services, LLC, Nashville, TN (US)

( * ) Notice: Subject to any disclaimer, the term of this patent is extended or adjusted under 35 U.S.C. 154(b) by 227 days.

This patent is subject to a terminal disclaimer.

(21) Appl. No.: 09/643,439

(22) Filed: Aug. 22, 2000

Related U.S. Application Data

(63) Continuation of application No. 09/299,311, filed on Apr. 26, 1999, now Pat. No. 6,205,356, which is a continuation of application No. 08/665,831, filed on Jun. 19, 1996, now Pat. No. 5,941,902.

(60) Provisional application No. 60/000,317, filed on Jun. 19, 1995, provisional application No. 60/000,300, filed on Jun. 19, 1995, provisional application No. 60/000,299, filed on Jun. 19, 1995, provisional application No. 60/000,318, filed on Jun. 19, 1995, and provisional application No. 60/001,012, filed on Jul. 10, 1995.

(51) Int. Cl.[7] .................................................. A61N 1/08
(52) U.S. Cl. ........................................... 607/3; 600/9
(58) Field of Search .............................. 607/3, 46, 48, 607/2; 600/9, 15

(56) References Cited

U.S. PATENT DOCUMENTS

| | | | | | |
|---|---|---|---|---|---|
| 4,232,680 | A | * | 11/1980 | Hundleson et al. | 128/422 |
| 4,233,965 | A | * | 11/1980 | Fairbanks | 128/1.5 |
| 4,454,883 | A | * | 6/1984 | Fellus | 128/422 |
| 4,556,051 | A | * | 12/1985 | Maurer | 128/1.5 |
| 5,312,321 | A | * | 5/1994 | Holcomb | 600/9 |
| 5,941,902 | A | * | 8/1999 | Holcomb | 607/3 |
| 6,205,356 | B1 | * | 3/2001 | Holcomb | 607/3 |

* cited by examiner

Primary Examiner—Jeffrey R. Jastrzab
Assistant Examiner—Frances P. Oropeza
(74) Attorney, Agent, or Firm—Garvey, Smith, Nehrbass & Doody, LLC; Gregory C. Smith

(57) ABSTRACT

A medical electronic apparatus for treating human pain by the application of an electrical stimulus with the proper current density and a special magnetic flux generator stimulus to the body surface of animals which includes an electrode complex of the treatment device which includes an adhesive means for holding the 4 electrodes of the device in contact with the human body. The electrode complex is preferably comprised of 4 electrodes which are 2 positive and 2 negative electrode defining opposite diagonal vertices of the quadrilateral shape. The electrodes are supplied by power means to activate and generate an electrical stimulus. Each electrode pad contains a Magna Bloc™ which snaps into position by an aluminum snap.

17 Claims, 10 Drawing Sheets

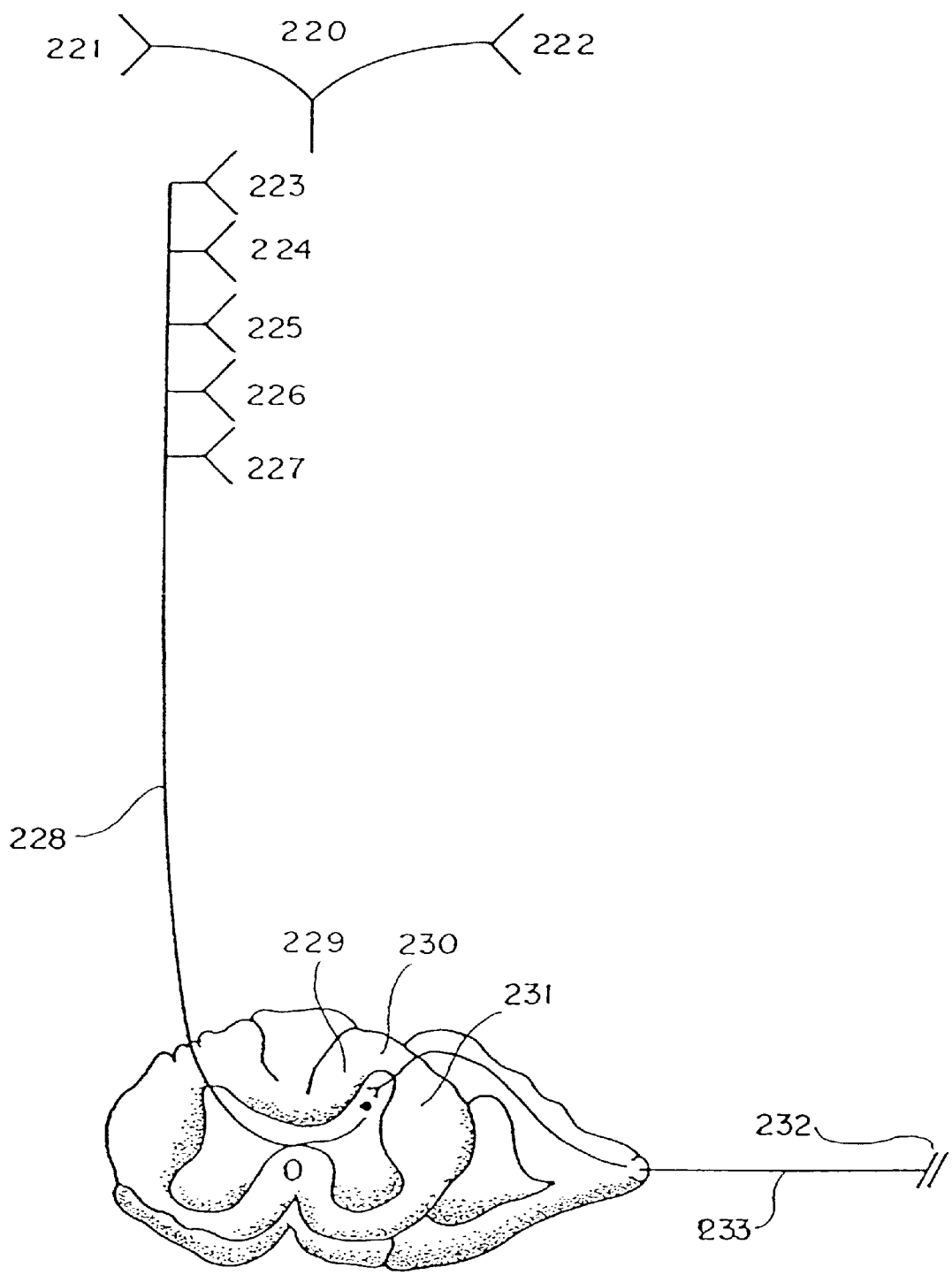
F I G . 7

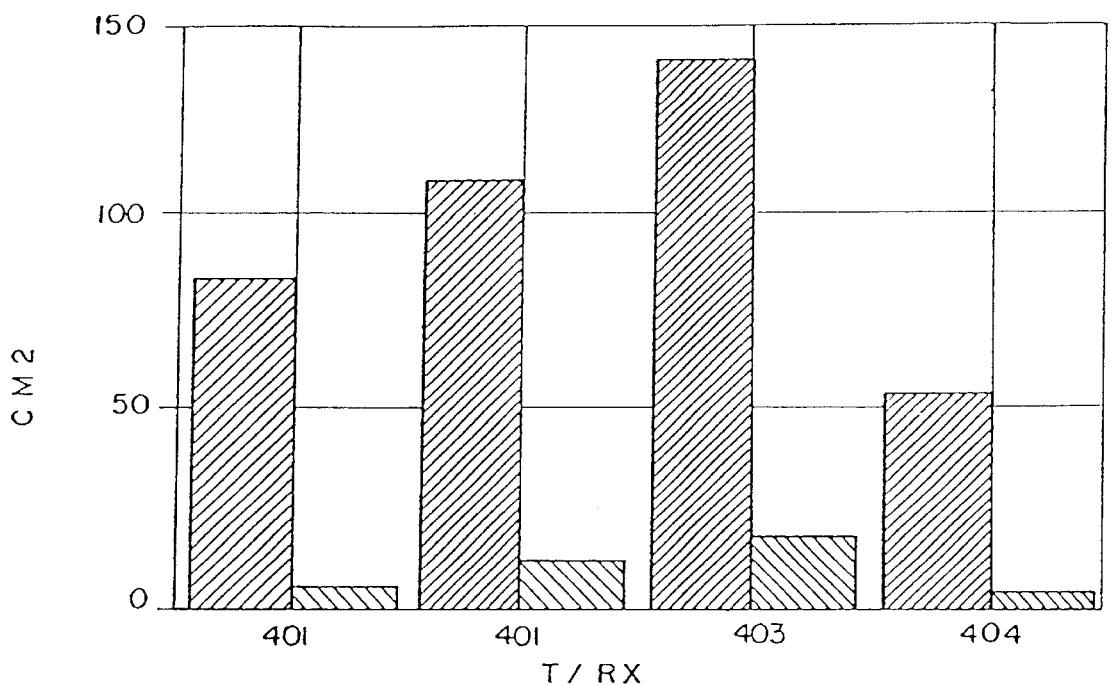
F I G. 9
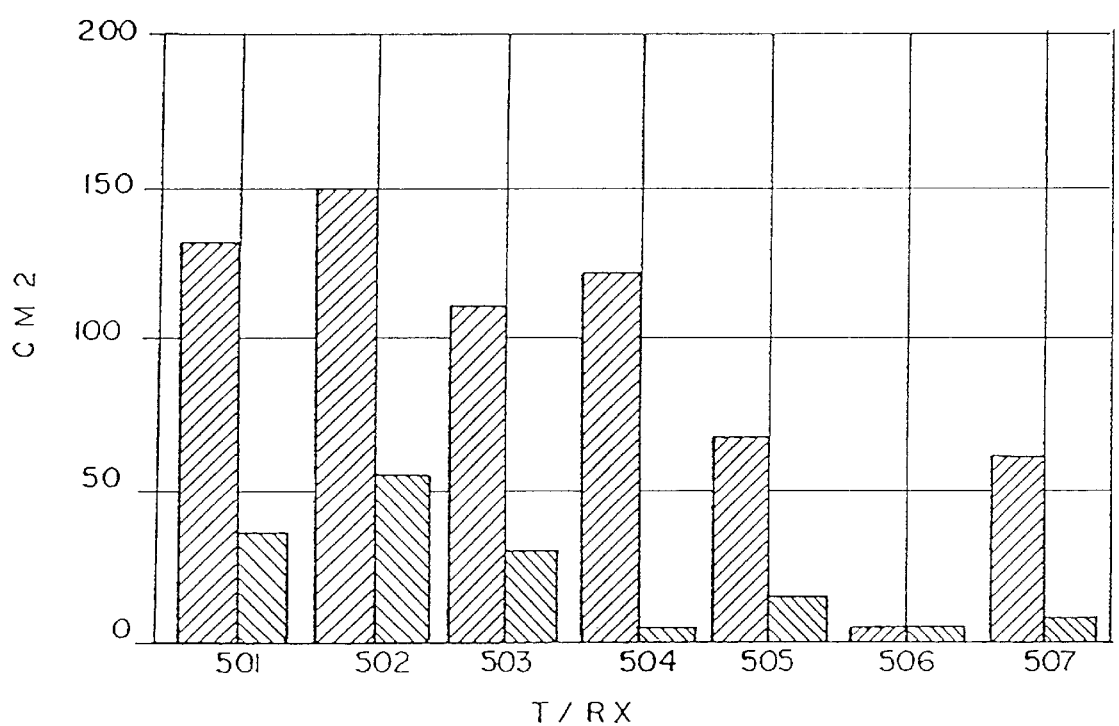
F I G. 10

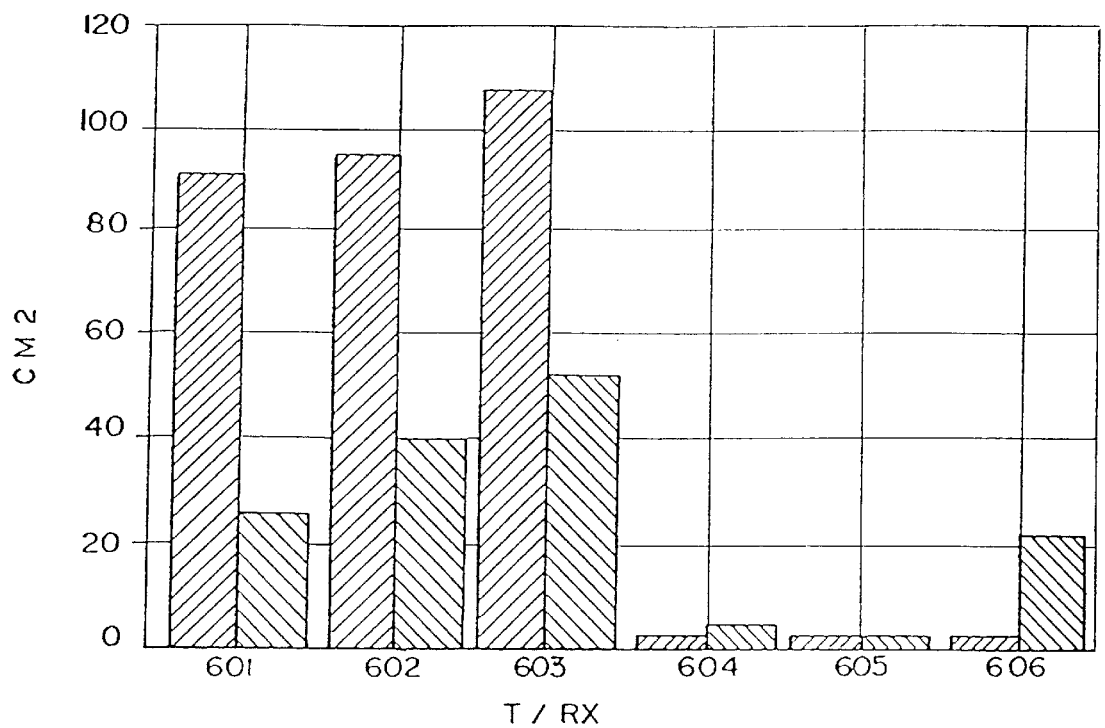
F I G. 11
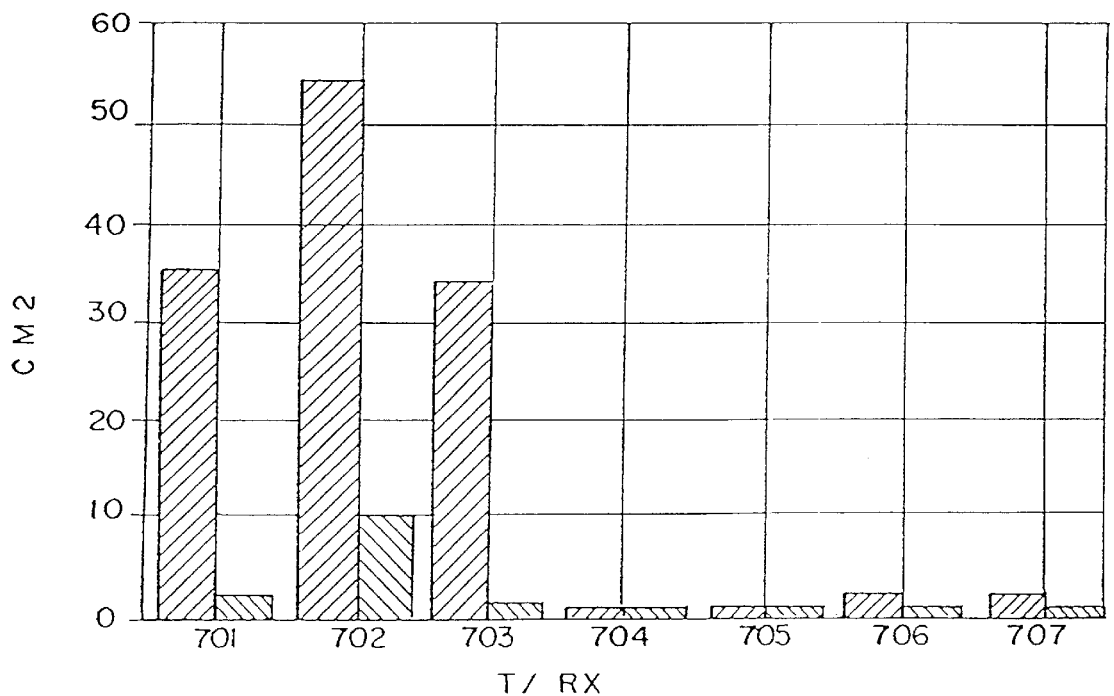
F I G. 12

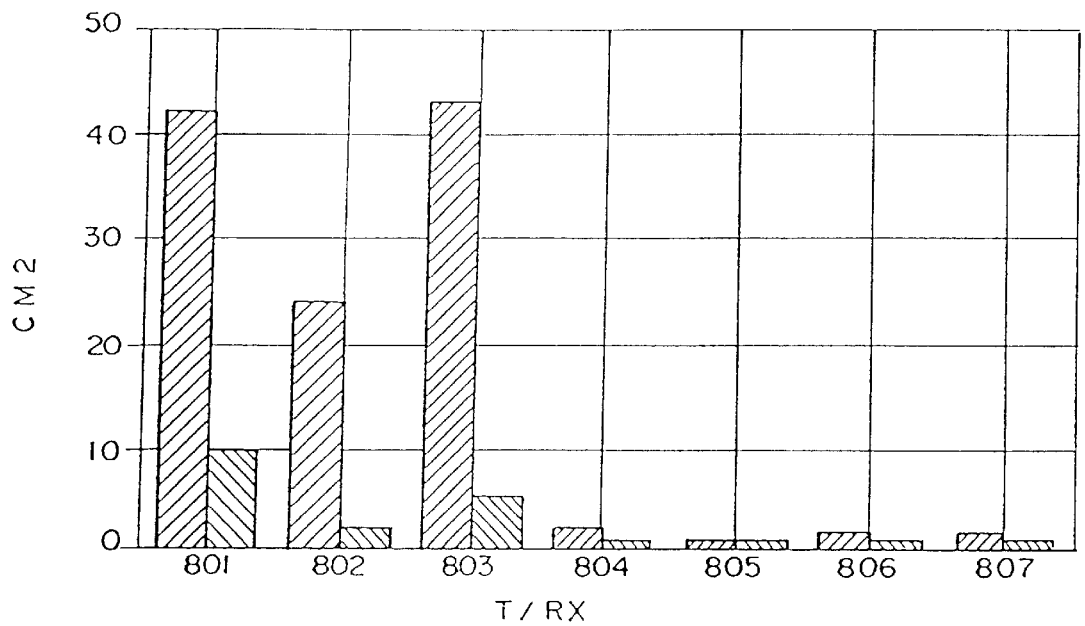
F I G. 13
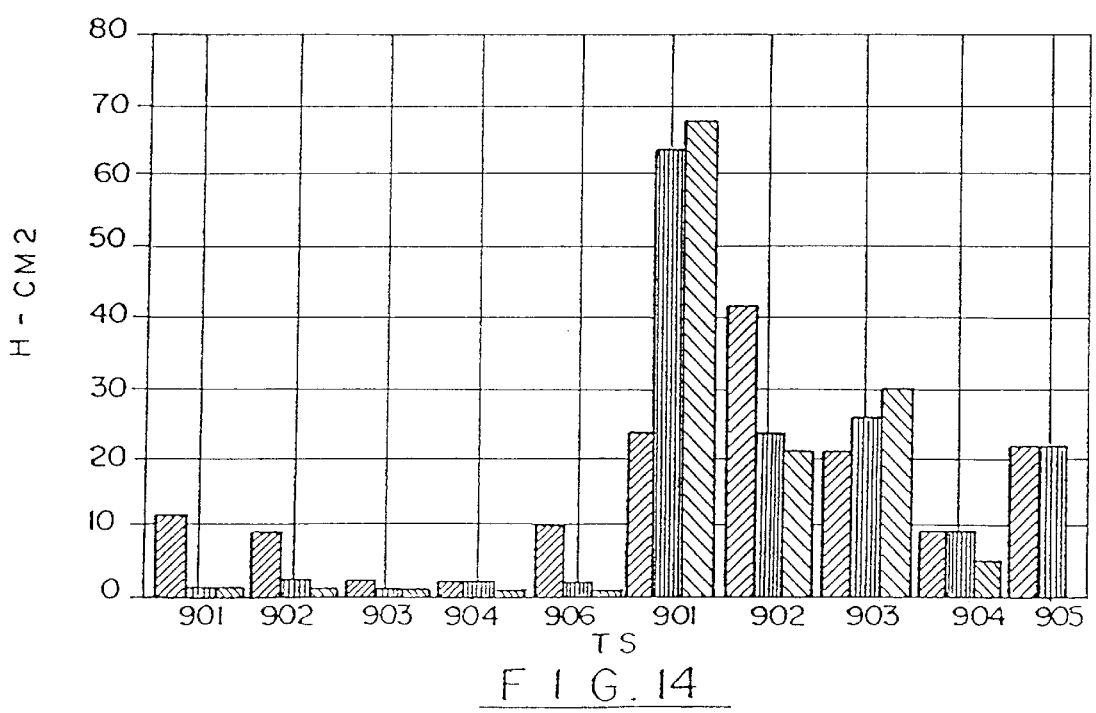
F I G. 14

ELECTRONIC APPARATUS AND METHOD FOR TREATING HUMAN PAIN THROUGH APPLICATION OF AN ELECTRICAL STIMULUS IN COMBINATION WITH APPLICATION OF A MAGNETIC FIELD

This is a continuation of U.S. patent application Ser. No. 09/299,311, entitled "An Improved Electronic Apparatus and method For Treating Human Pain Through Application of An Electrical Stimulus In Combination With Application of a Magnetic Field", filed Apr. 26, 1999, now U.S. Pat. No. 6,205,356 incorporated herein by reference. This application further incorporates by reference, is a continuation of, and claims priority to U.S. patent application Ser. No. 08/665,831, entitled "A Continuous Pulse, Non-Modulated Non-Burst Mode Nerve Stimulator and Method of Applying Same", filed Jun. 19, 1996, which has issued as U.S. Pat. No. 5,941,902, on Aug. 24, 1999. This application further incorporates by reference, and claims the priority of, U.S. Provisional Patent Application Serial No. 60/000,317, entitled "Treatment Device for Seizures and Cerebral Edema", filed Jun. 19, 1995; U.S. Provisional Patent Application Serial No. 60/000,300, entitled "Treatment Device for Cardiac Dysrhythmia", filed Jun. 19, 1995; U.S. Provisional Patent Application Serial No. 60/000,299; entitled "Treatment Device for Acute Burns", filed Jun. 19, 1995; U.S. Provisional Patent Application Serial No. 60/000,318, entitled "Method of Improving Efficacy and Sensory Tolerance With a Continuous Pulse, Non-Modulating Non-Burst Mode Nerve Stimulator", filed Jun. 19, 1995; and U.S. Provisional Patent Application Serial No. 60/001,012, entitled "Method of Inducing Regional Analgesia and/or Anesthesia With a Quadrapolar Static Magnetic Field Augmented by a Continuous Pulse, Non-Modulated Non-Burst Mode Nerve Stimulator", filed Jul. 10, 1995.

BACKGROUND OF THE INVENTION

Field of the Invention

This invention relates to the field of medical electronics and more particularly to apparatus for treating human pain by application of an electrical stimulus with the proper current density to the body surface and the response modulated by a magnetic field to allow manipulation of the firing rate of peripheral neurons of the A-fiber and C-fiber nociceptors such that chronic and acute pain may be consistently controlled without discomfort from the stimulation.

SUMMARY OF THE INVENTION

Maurer, et., al., 1994 (U.S. Pat. No. 4,431,002) indicates that it is well known that pain can be alleviated by electrical pulses applied to the surface of the body or to electrodes implanted within the body. His invention revealed a transcutaneous electrical nerve stimulation apparatus in which the stimulus pulses are modulated in both time and intensity in a prescribed manner, the pulse amplitude and width decreasing, while the pulse repetition rate increases and vice versa. The advantage of this arrangement is said to produce a comfortable and pleasant sensation at levels sufficient to produce muscle contraction and stimulation of deep afferent nerves to cause the release of endogenous opiates, such as endorphins, which are thought to suppress pain.

Deyo, et., al., (NEJM) concluded that Transcutaneous Electrical Nerve Stimulation (TENS) in patients with chronic low back pain is no more effective than treatment with placebo, and TENS adds no apparent benefit to that of exercise alone. It is apparent that such studies are done without the proper application and use of the technology. It is further apparent that technology is needed that is easier to understand and use by the operator.

The reduction of efficacy of a C-fiber input by coactivation of mechanoceptive A-fibers is the principle underlying transcutaneous electrical nerve stimulation (TENS). The mechanism involved is referred to as the "Gate Control Theory of Pain Perception" (See FIG. 5). TENS involves electrical activation of mechanoceptive fibers. Mechanoceptive A-fibers are activated at lower electrical stimulation intensities than C-fibers, that is, A-fibers have a low threshold. Thus, the mechanoceptive A-fibers can be selectively activated by low intensity electrical stimulation without increasing the firing rate of C-fibers, that is, A-fibers can be selectively activated by low intensity electrical stimulation without increasing the firing rate of C-fibers. As the intensity of stimulation is increased, it is possible to activate both mechanoceptive and nociceptive fibers. Thus, there is a limit to how much stimulation can be applied in order for the current TENS to work. Patients who use TENS devices are fully aware that if they continue to increase the stimulus intensity, they have more pain, rather than less pain. The increasing pain with stimulation is because of C-fiber activation. In some cases, the intensity of stimulation required to achieve pain relief can be reduced simply by repositioning electrodes and reducing the current flux through tissues while still reaching A-fiber threshold. In other cases, it is not possible to achieve pain relief at sufficiently low intensities to selectively activate A-fibers. In these cases, pain may be increased and TENS is said to have failed. In these cases of failure, the information available suggests that TENS failure is largely due to inappropriate electrode placement and insufficient current flow or density at the point of desired stimulation.

Evidence from the literature, clinical observations and isolated neuronal cell preparation data suggest that efficacy of this device is best obtained by high frequency, continuous stimulation with high current density in the area of stimulation. Pacing of A-fibers along with simultaneous suppression of C-fiber firing provides reliable control of pain syndromes. For the efficacy of the invention to be realized, a quadripolar array of positive and negative electrodes are arranged in quadrilateral array such that the positive and negative electrodes are in the proper close proximity to one another such that high current density can be obtained in the area of the nerve fiber to be paced. It is a further object of this invention to suppress the firing rates of C-fibers while increasing the rate of A-fibers. This object is accomplished by placing a Magna Bloc™ device within the stimulating electrode. This device, as will be demonstrated later, dramatically controls and reduces C-fiber firing. This effect on C-fiber firing is dramatically illustrated in FIG. 6. Volunteer subjects perceived the pain threshold at two (2) times the voltage (which translates to current flow) when the Magna Bloc™ device was placed over the stimulating electrodes. Through this methodology, normal firing patterns can be sent to the central nervous system, frequency coded, for a sensation of comfort rather than pain.

The device of this invention consists of 4 electrodes per unit. The electrodes consist of 4 electrodes of alternating polarity and consist of 2 positive poles and 2 negative poles. The positive and negative poles of the electrode head are aligned in substantially a single plane and are oriented in a quadrilateral configuration with positive poles oriented diagonally opposite one another and negative poles oriented diagonally opposite one another. Built into each electrode is a Magna Bloc™ device U.S. Pat. No. 5,312,321

(incorporated herein by reference). This device allows maximal A-fiber stimulation without the discomfort of C-fiber pain and muscle contraction. The Magna Bloc™ controls the excitability of neuromuscular units and blocks C-fiber firing.

Another object of the invention is to maintain current density sufficient to send A-fiber impulses into the dorsal horn in the area of the innervation of the C-fibers involved in the pain syndrome, in sufficient density to block C-fiber input into the central nervous system. This is accomplished by placing electrodes in the correct proximity to each other using the Magna Bloc™ to control C-fiber firing when the intensity is turned up to above usual C-fiber threshold and by placing a current sensor in the midpoint between the 4 electrodes. This sensor will balance the current density by rotating monitoring of the 4 electrodes and compensating by changing the input such that current density or current flow in the skin remains constant. This circuit will have a range monitor and alarm system. Current flow will alternate every 2 seconds in electrodes in FIG. 1B to A and C to D, C to A and B to D.

It is a further purpose of this invention to have two or more such 4 electrode arrays per TENS unit.

Except as noted above, the unit uses standard TENS electronics with the following parameters: 1) the parameters are intensity of output is 0 to 100 mA, frequency 0 to 200 Hzt, pulse width 400 microseconds. The device is effective either over the dorsal columns or on afferent nerve bundle as well as over the area of pain sensation. The containment means to hold the 4 electrodes, 4 Magna Bloc™ devices and current density sensor and electrode pads provides a method of therapeutically placing an alternating electrode DC frequency modulated device on the human body to relieve pain, which has well controlled current density in which C-fiber firing is controlled by a Magna Bloc™ field which generates a flux field gradient in the "2" axis of 60° to 70°.

This aspect may further provide repetition of these steps for additional containment bodies for attachment to the human body at additional placement positions.

BRIEF DESCRIPTION OF THE DRAWINGS

FIG. 3 depicts useful locations for the placement of the electrodes of the invention.

FIG. 7 illustrates the schematic representation of anatomical connections associated with pain perception and FIGS. 8–14 illustrate graphical representations of treatment for pain on subjects.

DESCRIPTION OF THE PREFERRED EMBODIMENT

Figure 1:
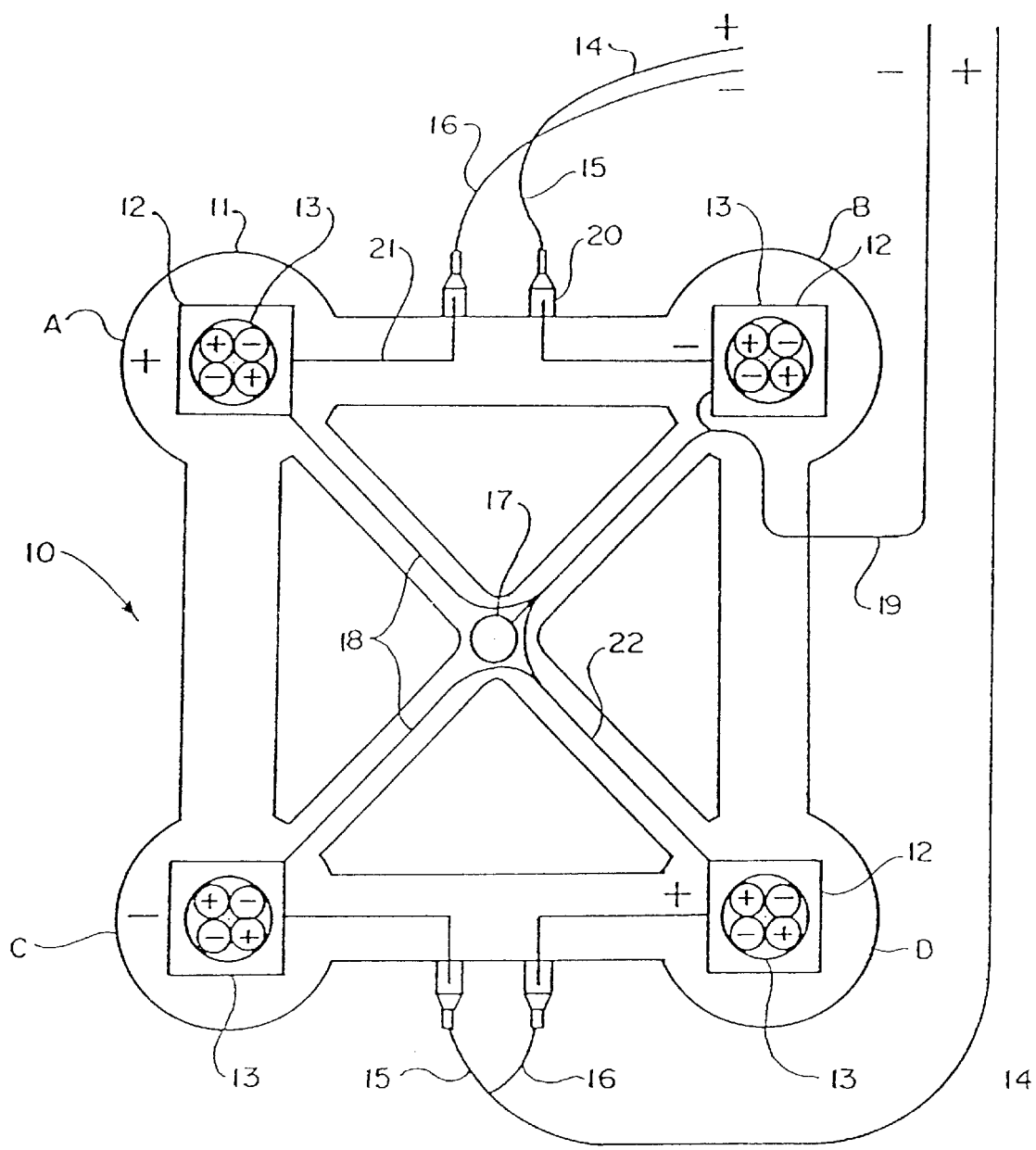
FIG. 1 is a prospective view of the treatment device electrodes according to one embodiment of the invention.

Reference will now be made in detail to the presently preferred embodiments of the invention, examples of which are illustrated in the accompanying drawings. Throughout the drawings, like reference characters are used to designate like elements.

The electrode complex of the treatment device of the current invention is schematically illustrated in FIG. 1. Treatment device electrode 10 includes an adhesive means 11 for holding the electrodes 12 and the Magna Bloc™ Devices 13 in contact with the human body. According to the invention, electrode 12 is preferably comprised of 4 electrodes, 2 of which are positive, 2 of which are negative and all of which are electrodes defining opposite diagonal vertices of the quadrilateral shape. Each electrode pad contains a Magna Bloc™ which snaps in position by an aluminum snap.

Figure 4:
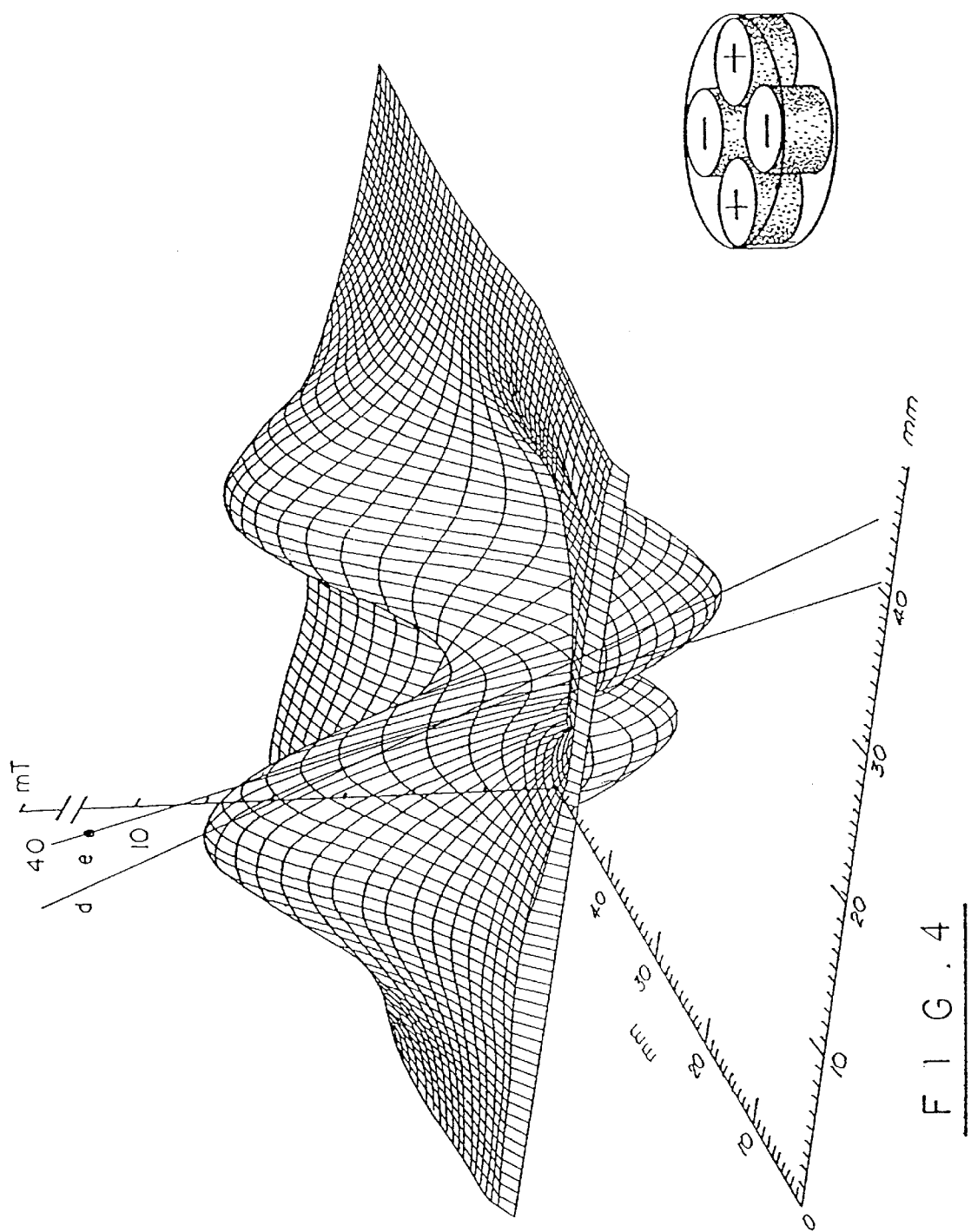
FIG. 4 depicts in graphic form field intensity of the magnetic quadripolar portion of the electrodes of the device, as determined by scanning in a systematic parallel plane 0.3 cm above the surface of the Magna Bloc™ m device.
Figure 5:
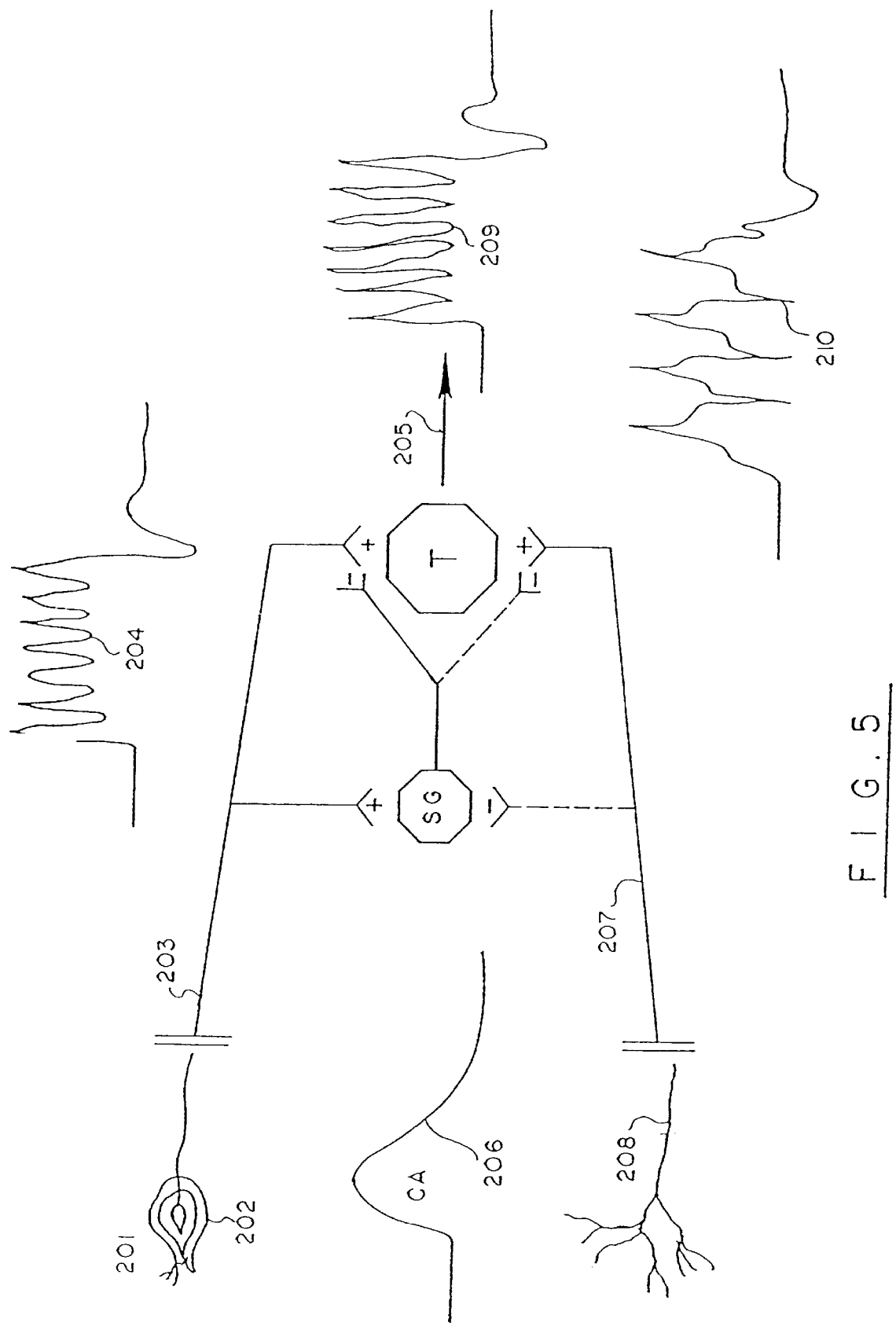
FIG. 5 is the Gate Theory of Pain Perception.

As embodied herein, Magna Bloc™ 13 (magnetic flux generator) comprises four substantially identical magnetic poles held in a plastic containment means that will hold the magnetic bodies in the desired configuration (see U.S. Pat. No. 5,312,321) and which produces a 60° to 70° gradient in the "z" axis (see FIG. 4). The gradient is the slope of the field intensity change over distance.

The embodiment of this invention further contains conducting wires 15 and 16 which connect to electrode wires 21 through connectors 20. The conducting wires 15 and 16 are contained in conducting cable 14. Further embodied in this invention is voltage sensor 17 with electrode connector cables 22 which are ultimately housed in conductor cable 19.

Figure 3:
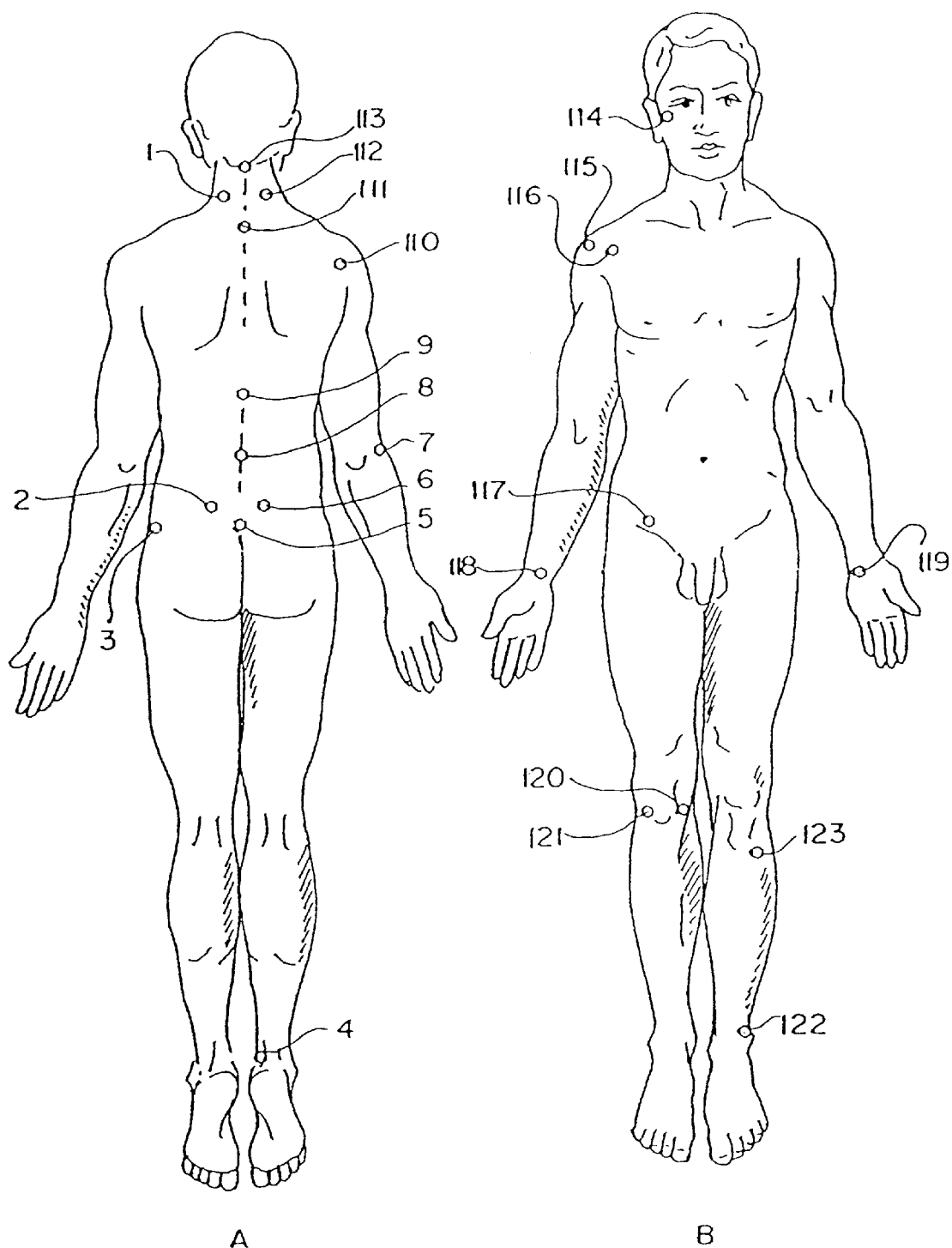
FIG. 3 is a block diagram of electrical stimulation apparatus according to the invention (fig. to follow).

The beneficial effects of this invention, as illustrated by FIGS. 8–14, are brought about by the ability of the system to maintain a proper current density or flow between the electrodes on a continuous basis in the area of the A-fibers and C-fibers involved in the pain syndrome under treatment. The desired current density is maintained by the electrode pads 12 which are controlled by range monitor (within the housing) and alarm system. The intensity of the current flow will be dictated by a voltage sensor 17. The current flow will alternate every 2 seconds in electrodes B to A, C to D, C to A and B to D. The density of current flow can be operated at a much higher level than in the classic TENS due to the placement of the Magna Bloc™ device 13 within the electrode 12. The Magna Bloc™ 13 completely relieves the discomfort of C-fiber firing when the C-fiber threshold is exceeded. The Magna Bloc™ 13 blocks C-fiber firing, therefore giving a favorable balance to A-fiber/C-fiber ratio and therefore makes this device very effective in relieving pain (see position suggestions for treatment in FIG. 3). For the Magna Bloc™ to control C-fiber firing it must have a field gradient of >45°<90° in the "z" axis.

Figure 2:
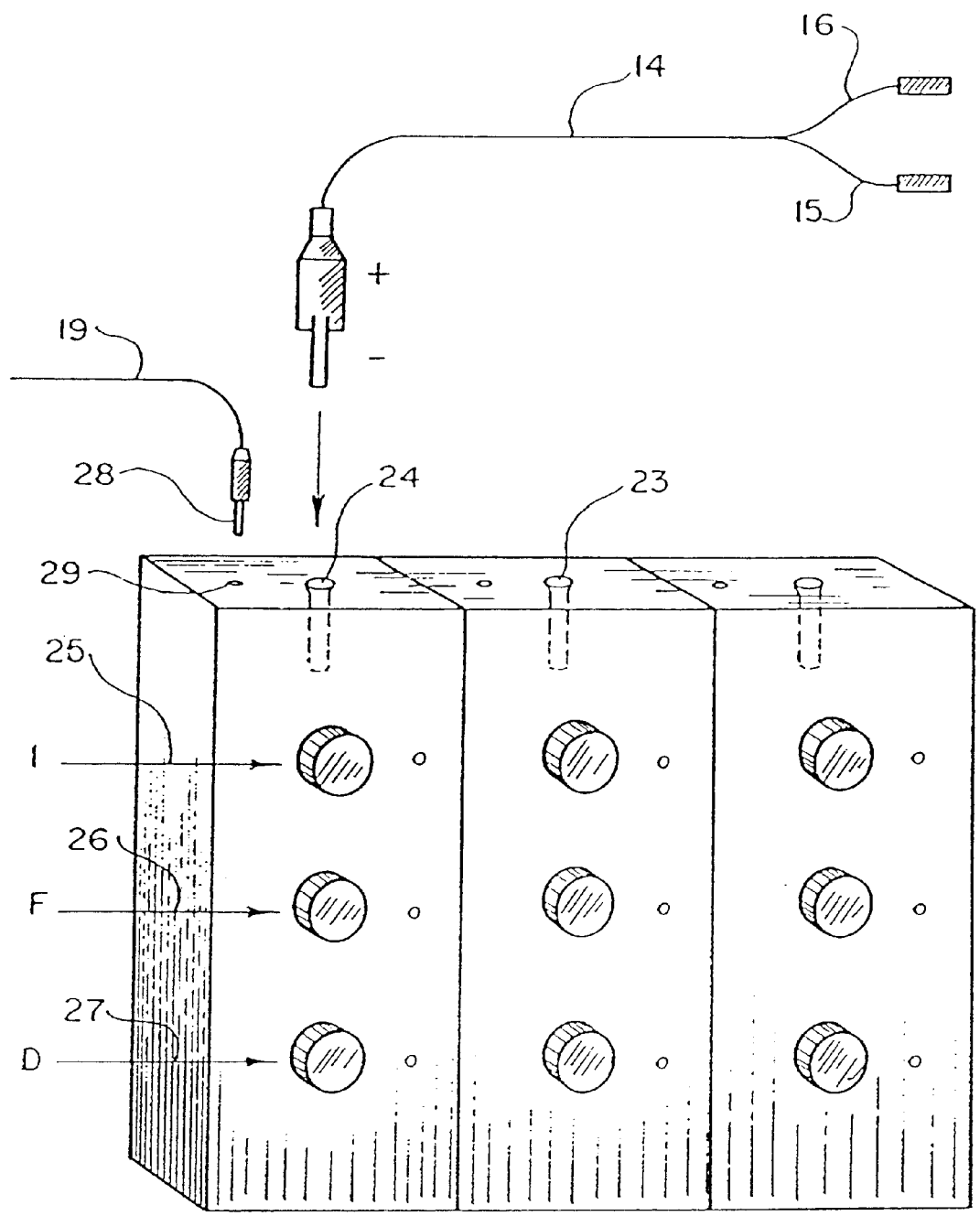
FIG. 2 is a plan view of the treatment device which powers the electrode of FIG. 1.

The controlling mechanism of this treatment device as shown in FIG. 2 contains a TENS generator unit 23 which contains the battery source, pulse generator, intensity controls 25, frequency controls 26, duration controls 27, current density modulation polarity switching means, current density modulation cable 19 with male connector 28 and female connector 29. Cable 14 male connector plugs into female connector 24. On-off and alarm light are contained within the cabinet housing.

Supporting Experimental Data

Table of Contents

I. INTRODUCTION
   a. Pain
   b. Pain Pathways and Pain Sensation
   c. Pain Impulse Generation II. METHODS OF INTERRUPTION OF PAIN IMPULSES
  a. Electrical Stimulation
  b. Magna Bloc™ TMNS
III. FIGURES
IV. APPENDIX Summary and Conclusions:

The data in this document demonstrates that the invention unit will block C-fiber mediated pain and hyperalgesia created by the intradermal injection of capsaicin in human volunteers as seen in FIGS. 8–14. This response is well documented by current density (current flow or density is calculated by the voltage from a stimulating electrode to any location of the treatment area, the resistance is calculated by an ohm circuit, with voltage and resistance—current density may be easily calculated) dose response curves as well as the demonstration that the area of hyperalgesia increases in size after the unit is turned off for five minutes (A-B-A observation). The Figures demonstrate the synergetic effect of the invention on a common pathway i.e. nociceptor input into the central nervous system.

I. INTRODUCTION

The data in this document demonstrates that the invention unit will block C-fiber mediated pain and hyperalgesia created by the intradermal injection of capsaicin in human volunteers. This response is well documented by current density (current flow or density is calculated by the voltage from a stimulating electrode to any location of the treatment area, the resistance is calculated by an ohm circuit, with voltage and resistance—current density may be easily calculated) dose response curves in the Figures as well as the demonstration in the Figures that the area of hyperalgesia increases in size after the unit is turned off for five minutes (A-B-A observation). The Figures demonstrate the synergetic effect of the invention on a common pathway i.e. nociceptor input into the central nervous system A. Pain. Pain is a multifactorial perception. The International Association for the Study of Pain defines pain as "unpleasant and emotional experience associated with actual or potential tissue damage."

B. Pain Pathways and Pain Sensation. The central nervous system integration of pain pathway stimulation takes place in the cerebral cortex. The Figures present a schematic representation of the anatomical connections associated with pain perception. The generation of the impulse usually begins in the peripheral nociceptors. The primary afferent neurons are largely A-delta and C-fibers. Pain intensity is related to the firing frequency of the impulses along the pathway. The various structures which have connections along the pain pathway affect the ultimate pain intensity and perception. Very complex circuits affect the pain perception involving both excitatory and inhibitory relationships.

C. Pain Impulse Generation. The Pain impulse (i.e. volley of action potentials) may be generated in the nerve ending (i.e. the receptor field) or anywhere along the pain pathway. Any stimulus or injury which results in repeated depolarization of the afferent neuron cell wall will result in a volley of action potentials which are conducted into the central nervous system.

II. METHODS OF INTERRUPTION OF THE PAIN IMPULSES

A. Electrical Stimulation. Various methods of electrical stimulation have been used in an attempt to control acute and chronic pain. The theories have largely included: 1)The Gate Control Theory and 2)The release of endorphins which block pain transmission. The most widely accepted is the Gate Control Theory. The reduction of efficacy of a C-fiber input by coactivation of mechanoceptive A-fibers thereby increasing the ratio of A-fiber/C-fiber is a principle mechanism. The net result is to increase the frequency of A-fiber firing to C-fiber firing. This results in a net decrease in nociceptor impulses into the central nervous system. Mechanoceptive A-fibers are activated at lower electrical stimulation intensities than C-fibers, that is, A-fibers have a low threshold. Thus, the mechanoceptive A-fibers can be selectively activated by low intensity electrical stimulation without increasing the firing rate of C-fibers. As the intensity of stimulation is increased, it is possible to activate both mechanoceptive and nociceptive fibers. This decreases the ratio of A-fiber to C-fiber firing and, as the stimulus intensity increases, the patient experiences more pain, rather than less, because of C-fiber activation and the decreasing A-fiber/C-fiber firing ratio. In some cases, it is not possible to achieve pain relief at sufficiently low intensities to selectively activate A-fibers. In these cases, pain may be increased with increased stimulus intensity and the TENS is said to have failed.

Figure 6:
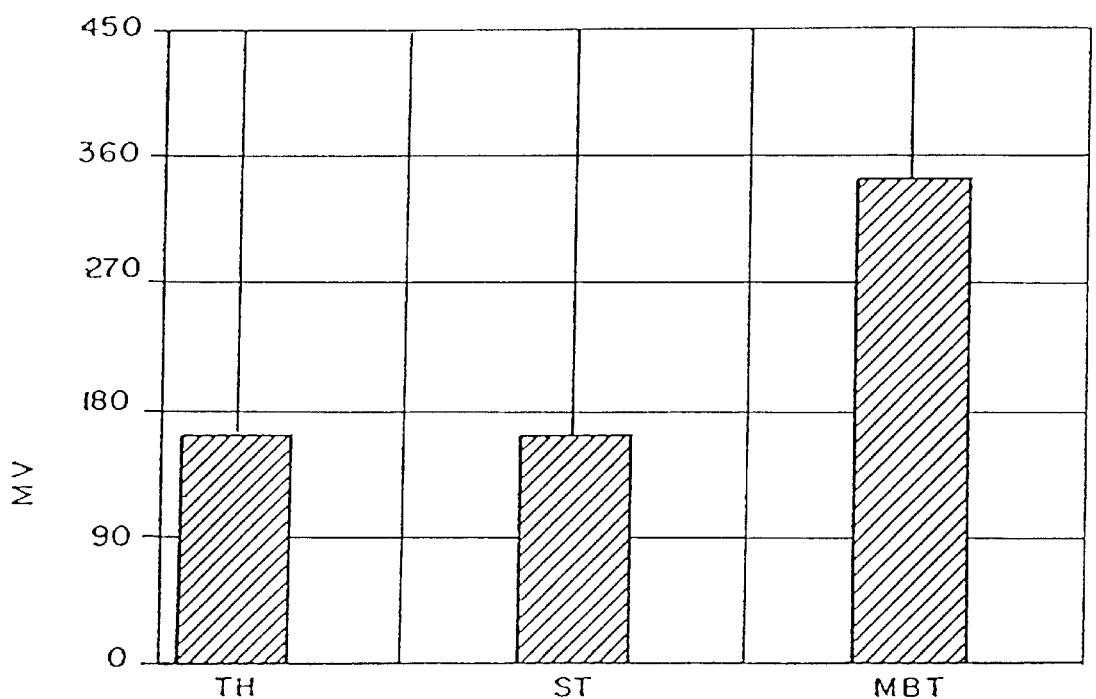
FIG. 6 is the change in somatosensory thresholds to electrical stimulus when treated with Magna Bloc™.
Figure 8:
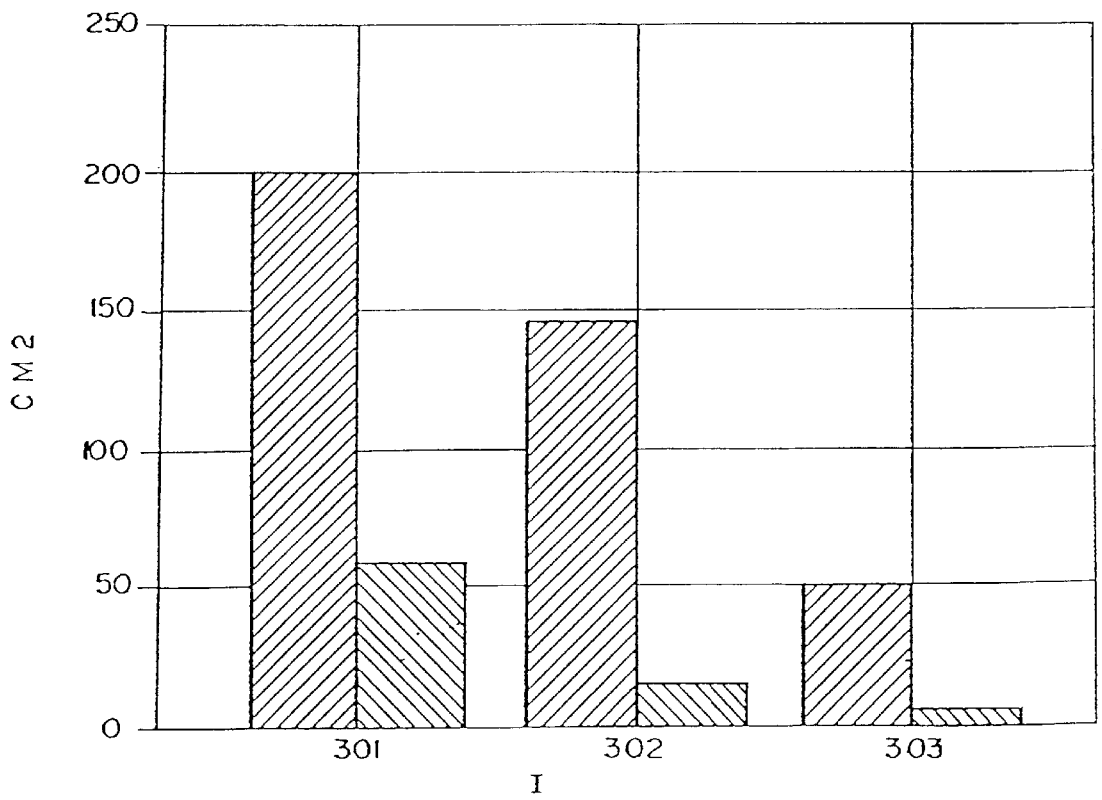

We have demonstrated that the mechanism of this invention involves blocking C-fiber nociceptor input into the central nervous system. We used the capsaicin model and demonstrated that the experimental unit blocks C-fiber mediated hyperesthesia and hyperalgesia (See FIGS. 8 through 14). FIG. 8 is a demonstration of the dose response of the area of capsaicin induced hyperalgesia and hyperesthesia with increasing current density. The area of hyperesthesia and hyperalgesia is expressed in $cm^2$ and the intensity is expressed as subthreshold, threshold and suprathreshold (see appendix). The notation of 60 m means stimulation for 60 minutes. FIG. 9 represents the change in surface hyperalgesia and hyperesthesia at threshold current for 15 minutes, 30 minutes, 60 minutes and for 5 minutes at suprathreshold. The remainder of the Figs. are self explanatory if reference is made to FIG. 8 or 9. FIG. 6 represents the evaluation of hyperalgesia at 15 minutes, 30 minutes, 60 minutes in both placebo and Magna Bloc™ treated arms, and the numbers 1 to 5 on the right are the same subjects (1-1, 2-2, 3-3, 4-4 and 5-5), but the opposite arm, which is placebo treated. We also demonstrated that the effect on blocking C-fiber transmission is related to current density in the area of pain generation. We have made the unit more effective by changes in electrode design and have demonstrated that the Gate Control mechanism is compatible with our findings.

Nociceptive C-fibers are ordinarily quiescent. However, a tissue-damaging stimulus activates free nerve endings imbedded in the dermis. This transducing step involves the influx of calcium to produce a generator potential. Once the generator potential reaches threshold, action potentials fire and are conducted centrally along C-fibers toward the spinal cord. The net result is that stimulation of C-fibers alters the ratio of A-fiber to C-fiber activation, which in turn increases the firing rate of the T cell and leads to pain perception, according to the Gate Control Theory of pain. The intensity of pain is proportional to the firing rate of the T cell. The invention has been shown to decrease the firing rate of C-fibers both in vitro and in vivo. The alteration in the ratio of A-fiber/C-fiber firing rate results in pain relief. B. Magna Bloc™ TMNS. Nociceptive C-fibers are ordinarily quiescent. However, a tissue-damaging stimulus activates free nerve endings imbedded in the dermis. This transducing step involves the influx of calcium to produce a generator potential. Once the generator potential reaches threshold, action potentials fire and are conducted centrally along C-fibers toward the spinal cord. The net result is that stimulation of C-fibers alters the ratio of A-fiber to C-fiber activation, which in turn increases the firing rate of the T cell and leads to pain perception, according to the Gate Control Theory of pain. The intensity of pain is proportional to the firing rate of the T cell. The Magna Bloc™ has been shown to decrease the firing rate of C-fibers both in vitro and in vivo. The alteration in the ratio of A-fiber/C-fiber firing rate results in pain relief in the same way in which the TENS brings about pain relief.

The Effects of Magna Bloc™ on C-Fibers which have been Stimulated by Capsaicin in Human Volunteers Introduction This report summarizes my analysis of the data collected in March, 1991 in a clinical study that was designed to test whether the treatment device of this application has a therapeutic effect on the human arm against which the device is applied. The tests were performed in conjunction with Jose Ochoa, M.D., Ph.D., DS.C. at Good Samaritan Hospital and Medical Center in Portland, Oreg. Dr. Ochoa is the Director of the Peripheral Nerve Disease Unit at Good Samaritan Hospital and Medical Center.

1. The clinical study was performed on five test subjects. Two of the test subjects were tested two times. The test subjects ranged from 37 to 50 years of age. Two subjects were female and three were male. Each of the test subjects was in good health. None of the test subjects were taking any medications.

2. The tests were conducted by a test investigator and a testing assistant. Each test subject was tested one time using an "active" magnetic treatment device (Magna Bloc™). The "active" treatment device used in the tests had four ½ inch diameter magnets, each having a magnetic energy product of 27 MG-Oe, all encased in an opaque plastic housing. Each test subject was also tested with a "placebo" device. The "placebo" device looked and felt identical to the "active" device, except in the placebo device, the four magnets were placed with four non-magnetic metal cylinders. The order of active or placebo testing was randomly selected by a coin toss. The test subject and test investigator did not know when a specific test was using the active device or the placebo device.

3. Each test subject was tested on one arm with the active magnetic treatment device and on the other arm with the placebo device. The arm allocation (right arm or left arm first) was randomly determined by a coin toss.

4. The following procedure was followed for each test, whether the right arm or left arm was tested and whether the treatment was active or placebo.

A. An injection point was identified on the volar forearm of the test subject 17.5 inches up the arm from the test subject's wrist. The injection point was marked with an ink dot. The treatment device (active or placebo) was centered over and against the injection point of the test subject's arm for 15 minutes. After 15 minutes, the treatment device was removed from the test subject's forearm and a 1 microgram dose of capsaicin was injected into the test subject's arm (intradermal) at the injection point.[1] Capsaicin is the pungent active component in hot chili peppers. Capsaicin has been found to activate the c-nociceptor nerve fibers in humans that convey painful stimuli to the central nervous system.

[1] One test subject showed no response to a I microgram dose of capsaicin and was accordingly injected with a 5 microgram dose of capsaicin.

B. Immediately following injection, the treatment device was placed back over the capsaicin injection point. At 15 minutes after the injection, the treatment device was removed briefly from the test subject's arm to permit measurement of the area of cutaneous hyperalgesia (skin pain due to light stroking with a cotton swab). Following this measurement, the treatment device was immediately placed back over the injection point. This procedure for measuring cutaneous hyperalgesia was repeated at 30 minutes after injection.

C. At 60 minutes after injection, the treatment device was removed from the test subject's arms and the area of cutaneous hyperalgesia was measured a third time. The area of hyperalgesia was measured at 15, 30 and 60 minutes after capsaicin injection. The area of hyperalgesia is determined by lightly stroking the skin with a cotton swab in a manner that would not ordinarily cause painful sensations. The area around the injection point where this light stroking caused pain to the test subject was traces and measured in square centimeters. The hyperalgesia area measurements for test subjects appear in the table (area of hyperalgesia).

5. Robert A. Parker is a biomedical statistician who has retained to analyze the data from the clinical study described above. Mr. Parker received a Bachelor of Science degree in Math from the Massachusetts Institute of Technology in 1970; received a Master of Science degree in Medical Statistics from the London School of Hygiene and Tropical Medicine in 1976; and received a Doctor of Science degree in Biostatistics from the Harvard School of Public Health in 1983. Mr. Parker is currently an Assistant Professor at the Vanderbilt University School of Medicine.

6. Mr. Parker found that the differences in results between active and placebo treatment were statistically significant for the measurements of area of hyperalgesia at 15, 30 and 60 minutes.

The Effects of TENS (Transcutaneous Electrical Nerve Stimulator) on Hyperesthesia and Hyperalgesia Mediated by C-fibers which have been stimulated by Capsaicin in Human Volunteers This report summarizes my analysis of the data collected in June 1995 at the Department of Neurology, Vanderbilt University Medical Center in Nashville, Tenn. The human study was designed to test whether the TENS device and the Magna Bloc™ device suppress or interrupt nociceptors (C-fibers) firing in a human pain model in which 1 microgram of capsaicin is injected intradermally and the area of mechanical hyperalgesia and hyperesthesia are evaluated with time. The purpose was to evaluate substantial equivalent mechanism of action.

1. The clinical study was performed on three (3) test subjects using both arms for the study. Variables were time, current density and combinations of TENS and Magna Bloc™. The test subjects ranged in age from 28 to 60 years. All test subjects were male and in good health. None of the subjects were taking any medications.

2. The tests were conducted by a test investigator and a testing assistant. We used an EPIX XL™ TENS unit with 4 electrodes for stimulation. The 4 electrodes of the TENS unit were placed over the corners of a 5 cm square. The polarity of each electrode was opposite to the electrode in the next corner and the same polarity as the electrode in the opposite corner. Each subject was tested one time using a TENS unit at subthreshold intensity in one arm and a TENS unit at threshold intensity followed by suprathreshold intensity in the other arm. Subthreshold level was defined as the minimal intensity perceived by the subject and Suprathreshold level was defined as the maximum intensity tolerated by the subject and described as discomfort, but not pain.

3. The following procedure was followed for each test.

A. An injection point was identified on the volar surface of the forearm of the test subject, 17.5 cm up the arm from the test subject's wrist. The injection point was marked with an ink dot. The treatment device was centered over the injection point of the test subject's arm for 15 minutes. After 15 minutes, a 1 microgram dose of capsaicin was injected on to the subject's arm (intradermal) at the injection point. Capsaicin is the pungent active component in chili peppers. Capsaicin has been found to activate the c-nociceptor nerve fibers in humans, resulting in pain and secondary hyperalgesia through a polysynaptic, reflex that convey painful stimuli to the central nervous system.

B. The areas of hyperesthesia (increased sensation to light touch by sliding over the skin the wood piece of a cotton swab) and hyperalgesia (skin pain to light touch by sliding over the skin the wood piece of a cotton swab) were measured at 15, 30 and 60 minutes after the injection of capsaicin and 5 minutes after the use of suprathreshold stimulation, Magna Bloc™. The areas of hyperesthesia and hyperalgesia were marked with ink lines and measured in square centimeter.

Capsaicin Model

Capsaicin is the "hot" or active portion of hot pepper. It has been demonstrated by multiple investigators that capsaicin, when injected into the skin intradermally, activates exclusively afferent polymodal (C-fiber) nociceptors. Therefore, C-fiber impulses into the central nervous system are perceived as pain. This C-fiber activation stimulates a spinal cord reflex which stimulates the sympathetic C-fiber efferents in the area of the capsaicin injection. C-fiber efferents overly sensitize the skin. The resultant effect is over sensitization of the skin which causes pain perception upon light touch. The area of hyperesthesia and hyperalgesia are related to C-fiber afferent firing rates. Therefore by use of this model one may evaluate the effect of treatment upon stimulation and conduction of painful impulses mediated by polymodal nociceptors.

The unit basically allows consistent results on pain treatment because of the ability to produce symmetric current density which is selective for stimulation of A-fiber and suppression of C-fibers. This unit is much more effective and comfortable.

What is claimed is:

1. A medical electronic apparatus for treating human pain by the application of an electrical stimulus with proper current density and a special magnetic flux generator stimulus, the apparatus comprising:
    a) an electrode complex of a treatment device comprising electrodes and an adhesive means for holding the electrodes in contact with the human body;
    b) wherein the electrodes further comprise positive and negative electrodes defining opposite diagonal vertices of a quadrilateral shape and defining an electrode pad;
    c) power means for supplying power to activate an electrical stimulus to each electrode;
    d) the electrode pad further comprising at least one quadrapolar magnetic flux generator having four center charged magnetic poles in alternating polarity for generating a three-dimensional flux field gradient >45 degrees <90 degrees in the "Z" axis.

2. The therapeutic medical electronic apparatus of claim 1, wherein each electrode comprises the at least one quadrapolar magnetic flux generator having four center charged magnetic poles in alternating polarity for generating a three-dimensional flux field gradient >45 degrees <90 degrees in the "Z" axis in modulating C-fiber activity.

3. The therapeutic medical electronic apparatus of claim 2, wherein the quadrapolar magnetic flux generator is composed of 4 circular, center charged, neodymium magnetic poles in alternating polarity.

4. The therapeutic medical electronic apparatus of claim 2, wherein each magnetic flux generator of the invention comprises four substantially identical magnetic poles held in a plastic containment means that will hold the magnetic bodies in the desired configuration and which produces a 60° to 70° magnetic flux field gradient in the "Z" axis.

5. A medical electronic apparatus for treating human pain by application of an electrical stimulus, the apparatus comprising:
    a) an electrode complex comprising at least one electrode that is adapted to be in contact with a human to be treated; wherein the electrode further comprises positive and negative electrodes to finding opposite diagonal vertices of a quadrilateral shape and defining an electrode pad.
    b) each electrode further comprising at least one quadrapolar magnetic flux generator having four center charged magnetic poles in alternating polarity for generating a three-dimensional flux field gradient >45 degrees <90 degrees in the "Z" axis; and
    c) power means for supplying power to activate an electrical stimulus to each electrode for the purpose of modulating C-fiber activity.

6. The apparatus of claim 5, comprising a plurality of electrodes that are adapted to be in contact with the body surface of a human to be treated.

7. The apparatus of claim 5, comprising four electrodes that are adapted to be in contact with the body surface of a human to be treated.

8. The apparatus of claim 6 or 7, wherein each electrode further comprises a plurality of quadrapolar magnetic flux generators having four center charged magnetic poles in alternating polarity for generating a three-dimensional flux field gradient >45 degrees <90 degrees in the "Z" axis.

9. The apparatus of claim 7 wherein the electrodes are placed at a sufficient distance apart from a person to be treated to allow for the proper current density in the field of stimulation when electrical stimulus is applied thereto.

10. The apparatus of claim 7 wherein the electrode complex further comprises a single contiguous unit which includes an adhesive means for holding the electrodes in contact with the body surface.

11. The apparatus of claim 5 wherein each quadrapolar magnetic flux generator defines a means for suppressing C-fiber firing, thereby allowing a favorable ratio of A delta/C-fiber firing and thereby more efficiently blocking peripheral generated pain.

12. The apparatus of claim 5, wherein each magnetic flux generator comprises four circular, center charged, neodymium magnetic poles.

13. The apparatus of claim 5, wherein each magnetic flux generator generates a three-dimensional flux field gradient >60 degrees <70 degrees in the "Z" axis.

14. The apparatus of claim 5, further comprising a means for alternating current flow to each electrode every 2 seconds.

15. The apparatus of claim 5, further comprising a range monitor and alarm system, the range monitor and alarm system receiving sensory input data from a voltage sensor in contact with the body surface and controlling current density from the sensory input.

16. The apparatus of claim 15, wherein the range monitor and alarm system maintains a proper current density on a continuous basis for the purpose of modulating A-fiber and C-fiber activity.

17. The apparatus of claim 5, further comprising a TENS generator unit operatively connected to the electrode complex, the TENS generator unit further comprising a battery supplying power to the unit, a pulse generator creating a pulsed electrical current through the unit, means for controlling current intensity, density, frequency and duration through the electrode complex; and means for modulating current density and alternating current direction through the electrode complex.

* * * * *